US006232116B1

(12) United States Patent
Briles et al.

(10) Patent No.: US 6,232,116 B1
(45) Date of Patent: *May 15, 2001

(54) ORAL ADMINISTRATION OF PNEUMOCOCCAL ANTIGENS

(75) Inventors: David E. Briles, Birmingham, AL (US); Larry S. McDaniel, Ridgeland, MS (US); Masafumi Yamamoto; Hiroshi Kiyono, both of Birmingham, AL (US)

(73) Assignee: University of Alabama at Birmingham Research Foundation, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/482,981

(22) Filed: Jun. 7, 1995

Related U.S. Application Data

(63) Continuation-in-part of application No. 08/458,399, filed on Jun. 2, 1995, and application No. 08/446,201, filed on May 19, 1995, which is a continuation-in-part of application No. 08/312,949, filed on Sep. 30, 1994, which is a continuation-in-part of application No. 08/246,636, filed on May 20, 1994, which is a continuation-in-part of application No. 08/048,896, filed on Apr. 20, 1993, now abandoned, which is a continuation-in-part of application No. 07/835,698, filed on Feb. 12, 1992, now abandoned, which is a continuation-in-part of application No. 07/656,773, filed on Feb. 15, 1991, now abandoned.

(51) Int. Cl.$^7$ ............................. A61K 39/09; C12N 15/00

(52) U.S. Cl. ..................................... 435/320.1; 424/244.1

(58) Field of Search ....................... 424/244.1; 435/320.1

(56) References Cited

U.S. PATENT DOCUMENTS

| 4,873,090 | * | 10/1989 | Clancy et al. ........................ 424/451 |
| 5,182,109 | * | 1/1993 | Tamura et al. ......................... 424/92 |
| 5,476,929 | * | 12/1995 | Briles et al. ....................... 536/24.32 |

FOREIGN PATENT DOCUMENTS

| 9214488 | 9/1992 | (WO) ........................... A61K/39/12 |

OTHER PUBLICATIONS

Abbas, A.K., Lichtman, A.H., Pober, J.S., In Cellular and Molecular Immunology, ed. Wonsiewicz M., (W.B. Saunders Co., Philidelphia) (1991). No Articles.
Abraham, E., Robinson, A., Vaccine 9:757–764 (1991).
Anastassiou, E.D., Yamada, H., Francis, M.L., Mond, J.J., Tsokos, G.C., J. Immunol. 145:2375–2380 (1990).
Andersson, B., Eriksson, B., Falsen, E., Fogh, A., Hansen, A., Nylen, O., Peterson, H., and Svanborg–Eden, C., Infect. Immun. 32:311–317 (1981).
Anonymous. Centers for Disease Control HIV/AIDS Surveillance Report, Aug. :1–18 (1991).
Bale, J.R., Rev. Infect. Dis. 12 (Suppl 8):S861–S1083 (1990).

Barbour, M.L., Mayon–White, R.T., Crook, D.W., Coles, C., Moxon, E.R., ICAAC Abstracts 33:175 (1993).
Berman, S., McIntosh, K., Rev. Infect. Dis. 7:647–691 (1985).
Bessen, D., Fischetti, V.A., Infect. Immun. 56:2666–2672 (1988).
Bienenstock, J., Johnston, N., Perey, D.Y., Lab. Invest. 28:686–692 (1973a).
Bienenstock, J., Johnston, N. Perey, D.Y., Lab. Invest. 28:693–698 (1973b).
Bohr, V., Rasmussen, N., Hansen, B., Gade, A., Kjersem, H., Johsen, N., Paulson, O., J. Infect. Dis. 10:143–157 (1985).
Bolan, G., Broome, C.V., Facklam, R.R., Plikaytis, B.D., Fraser, W.D., Schlech, W.F.I., Ann. Intern. Med. 104:1–6 (1986).
Briles, D.E., Crain, M.J., Gray, B.M., Forman, C., Yother, J., Infect. Immun. 60:111–116 (1992).
Briles, D.E., Claflin, J.L., Schroer, K., Forman, C., Nature 294:88–90 (1981).
Briles, D.E., Forman, C., Horowitz, J.C., Volanakis, J.E., Benjamin, W.H. Jr., McDaniel, L.S., Eldridge, J., Brooks, J., Infect. Immun. 57:1457–1464 (1989).
Brimblecombe, F.S.W., Cruicshank, R., Masters, P.L., Reid, D.D., Stewart, G.T., British Medical Journal :119–128 (1958).
Bromander, A., Holmgren, J., Lycke, N., Journal of Immunology 146:2908–2914 (1991).
Chen, K–S., Strober, W., Eur. J. Immunol., 20:433–436 (1990).
Chiu, S.S., Greenberg, P.D., Marcy, S.M., Wong, V.K., Chang, S.J., Chiu, C.Y., Ward, J.I., Pediatric Res. Abstracts 35:10A (1994).
Converse, G.M. III, Dillon, H.C. Jr., J. Clin. Micro. 5:293–296 (1977).
Cowan, M.J. Ammann, A.J., Wara, D.W., Howie, V.M., Schultz, L., Doyle, N., Kaplan, M., Pediatrics 62:721–727 (1978).
Croitoru, K., Bienenstock, J., In Handbook of Mucosal Immunology, ed. Ogra, P.L., Mestecky, J., Lamm, M.E., Strober, W., McGhee, J.R., Bienenstock, J., (Acamdemic Press, Inc., San Diego, CA) pp. 141–149 (1994).

(List continued on next page.)

Primary Examiner—James C. Housel
Assistant Examiner—Rodney P Swartz
(74) Attorney, Agent, or Firm—William S. Frommer; Thomas J. Kowalski; Frommer Lawrence & Haug LLP

(57) ABSTRACT

Oral or peroral administration, including intragastrically, of killed whole pneumococci, lysate of pneumococci and isolated and purified PspA, as well as immunogenic fragments thereof, particularly when administered with an adjuvant such as cholera toxin provides protection in a host, animal or human, against pneumococcal infection, including colonization, and systemic infection, such as sepsis. The ability to elicit protection against pneumococcal colonization in a host prevents carriage among immunized individuals, which can lead to elimination of disease from the population as a whole.

14 Claims, 2 Drawing Sheets

OTHER PUBLICATIONS

Czerkinsky, C., Russell, M.W., Lycke, N., Lindbald, M., Holmgren, J., Infect. Immun. 57:1072–1077 (1989).

Czerkinsky, C., Nilsson, L–A., Nygren, H., Ouchterlony, O., Tarkowksi, A., J. Immunol. Methods 65:109–121 (1983).

Dagen, R., Melamed, R., Abranson, O., Piglansky, L., Greenberg, D., Mendelman, P.M., Bohidar, N., Ter–Minassian, D., Cvanovich, N., Lov, D., et al., Pediat. Res. 37:172A (1995).

de Vos, T., and Dick, T.A., J. Immunol. Med. 141:285–288 (1991).

DeMaria, T.F., McGhee, R.B., Lim, D.J., Arch. Otolaryngol. 110:279–280 (1984).

Dillard, J.P. and Yother, J., Molec. Microbiol. 12:959–972 (1994).

Douglas, R.M., Miles, H.B., Paton, J.C., American Journal of Diseases of Children 140:1183–1185 (1986).

Douglas, R.M. Miles, H.B., Journal of Infectious Diseases 149:861–869 (1984).

Elson, C.O., Curr. Topics Microbiol. Immunol. 146:29–33 (1989).

Elson, C.O., Ealding, W., J. Immunol. 132:2736–2741 (1984).

Elson, C.O., Holland, S.P., Dertzbaugh, M.T., Cuff, C.F., A.O., Anderson, J. Immunol. 154:1032–1040 (1995).

Fallon, M.T., Reinhard, M.K., Gray, B.M., Davis, T.W., Lindsey, J.R., Laboratory Animal Science 38:129– (1988).

Francis, M.L., Ryan, J., Jobling, M.G., Holmes, R.K., Moss, J., Mond. J.J., Journal of Immunology 148:1999–2005 (1992).

Fraser, D.W., In Bacterial Vaccines, ed. JB Robbins, Hill JC, Sadoff JC, (New York) xix–xxiv (1982).

Garrone, P., Banchereau, J., Moleuclar Immunology 30:627–635 (1993).

Gizurarson, S., Tamura, S., Kurata, T., Hasiguchi, K., Ogawa, H., Vaccine 9:825–832 (1991).

Gotschlich E.C., Goldschneider, I., Lepow, M.L., Gold, R., In Antibodies in human diagnosis and therapy (Raven, New York) pp. 391–402 (1977).

Gratten M. Naraqi, S., Hansman, D., Lancet ii:192–195 (1980).

Gray, B.M. Converse G.M. III, Dillon, H.C., J. Infect. Dis. 142:923–933 (1980).

Gray, B.M., Converse, G.M. III. Huhta, N., Johnston, R.B. Jr., Pichichero M.E., Schiffman, G., Dillon, H.C. Jr., J. Infect. Dis. 142:312–318 (1981).

Greenwood, B.M., Greenwood A.M., Bradley, A.K., Tulloch, S., Hayes, R., Oldfield, F.S.J., Ann. Trop. Pediatr. 7:91–99 (1987).

Gwaltney, J.W., Sande, M.A., Austrian, R., et al., J. Infect. Dis. 132:62 (1975).

Haack, B.M., Emmrich, F., Resch, K., Journal of Immunology 150:2599–2606 (1993).

Hakansson, A., Kidd, A., Wadell, G., Sabharwal, H., and Svanborg, C., Infect. Immun. 62:2707–2714 (1994).

Hendley, J.O., Sande, M.A., Stewart, P.M., et al., J. Infect. Dis. 132:55 (1975).

Hollingshead, S.K., Simecka, J.W., Michalek, S.W., Infect. Immun. 61:2277–2283 (1993).

Kauppi, M., Eskola, J. Kathty, H.H., ICAAC Abstracts 33:174 (1993).

Klein, J.O., Rev. Infect. Dis. 3:246– (1981).

Klugman, K.P., Clin. Microbiol. Rev. (1990).

Kuper, C.F., Koornstra, P.J., Hameleers, D.M.H., Biewenga, J., Spit, B.J., Duijvestijn, A.M., van Breda Vriesman, P.J.C., Sminia, T., Immunol. Today 13:219–224 (1992).

Liang, X., Lamm, M.E., Nedrud, J.G., Journal of Immunology 141:1495–1501 (1988).

Lock, R.A., Hansman, D., Paton, J.C., Microbial Pathogenesis 12:137–143 (1992).

Lock, R.A., Paton, J.C., Hansman, D., Microb. Pathog. 5:461–467 (1988).

Lycke, N., Holmgren, J., Immunology 59:301–308 (1986).

Lycke, N., Strober, W., J. Immunol. 142:3781–3787 (1989).

Lycke, N., Karlsson, U., Sjölander, A., Magnusson, K–E., Scand. Journal of Immunology 33:691–698 (1991).

Lycke, N., Tsuji, T., Holmgren, J., European Journal of Immunology 22:2277–2281 (1992).

Marton, A., Gulyas, M., Munoz, R. Tomasz, A., J. Infect. Dis. 163:542–548 (1991).

Masters, P.L., Brumfitt, W., Mendez, R.L., Likar, M., Brit. Med. J. 1:1200–1205 (1958).

Mestecky, J., J. Clin. Immunol. 7:265–276 (1987).

Munoz, R., Musser, J.M., Crain, M. Briles, D.E., Marton, A., Parkinson, A.J., Sorensen U., Tomasz, A., Clinic Infect. Dis. 15:112–118 (1992).

Muñoz, E., Zubiaga, A.M., Merrow, M., Sauter, N.P., Huber, B.T., J. Exp. Med. 172:95–103 (1990).

Quiding, M., Nordstrom, I., Kilander, A., Anderson, G., Hansen, L.A., Holmgren, J., Czerkinsky, C., J. Clin. Invest. 88:143–148 (1991).

Russell, M.W., Prince, S.J., Ligthart, G.J., Mestecky, J., Radl, J., Aging Immunol. Infect. Dis. 2:275–286 (1990).

Russell, M.W., Wu, H–Y., Infection and Immunity 59:4061–4070 (1991).

Shapiro, E.D., Berg, A.T., Austrian, R., Schroeder, D., Parcells, V., Margolis, A., Adair, R.K., Clemmens, J.D., N. Engl. J. Med. 325:1453–1460 (1991).

Smillie, W.G., Am. J. Hyg. 24:522–535 (1936).

Smillie, W.G., Warnock, G.H., White, H.J., Am. J. Pub. Hlth. 28:293–302 (1938).

Spika, J.S., Munshi, M.H., Wojtyaniak, B., Sack, D.A. Hossain, A., Rahman, M., Saha, S.K., Ann. Trop. Pediatr. 9:33–39 (1989).

Svernerholm, A.M., Jertborn, M., Gothefors, L., Karim, A.M.M.M., Sack, D.A., Holmgren, J., J. Infect. Dis. 149:884–893 (1984).

Szu, S.C., Li, X., Schneerson, R., Vickers, J.H., Bryla, D., Robbins, J.B., Infect. Immun. 57:3823–3827 (1989).

Wilson, A.D., Clarke, C.J., Stokes, C.R., Scand. J. Immunol. 31:443–451 (1990).

Wilson, A.D., Stokes, C.R., Bourne, F.J., Scand. J. Immunol. 29:739–745 (1989).

Wilson, A.D., Bailey, M., Williams, N.A., Stokes, C.R., European Journal of Immunology 21:2333–2339 (1991).

Woogen, S.D., Ealding, W., Elson, C.O., Journal of Immunology 139:3764–3770 (1987).

Wu, H–Y, Russell, M.W., Infection and Immunity 61:314–322 (1993).

Ziegler–Heitbrock, H.W.L., Passlick, B., Kafferiein, E., Coulie, P.G., Izbicki, J.R., Infect. Immun. 60:1692–1694 (1992).

Jackson, R.J., et al., Infect. Immun. 61: 4272–4279 (1993).

Xu–Amano, J., et al., J. Exp. Med. 178: 1309–1320 (1993).

Xu–Amano, R.J., et al., Vaccine 12: 903–911 (1994).

McGhee, J.R., et al., Inf. Agents Dis. 2: 55–73 (1993).

Yothen et al Abstracts of the General Meeting of the ASM, p. 127, D–189, 1992.*

Yoshimura et al Abstracts of the fifth International Symposium, Recent Advances in Otitis Media, p. 73, Abst #77.*

Germie et al Novel Vaccine Strategies Mucosal Immunization, Adjuvants & Genetic Approaches Oct. 1993.* van de Wijgent et al Infection & Immunity 59:2750–2757, 1991.*

Bixlen Synthetic Vaccines vol. 1 pp. 39–71.*

Ozenkinsky et al Infection & Immunity 57:1072–1077, 1989.*

Kurono et al Abstracts of the Fourteenth Midwinter Research Meeting Association for Research in Otolaryngology p. 56, Abst#178 1991.*

McDaniel et al, Infection & Immunity 59:222–228 1991.*

* cited by examiner-

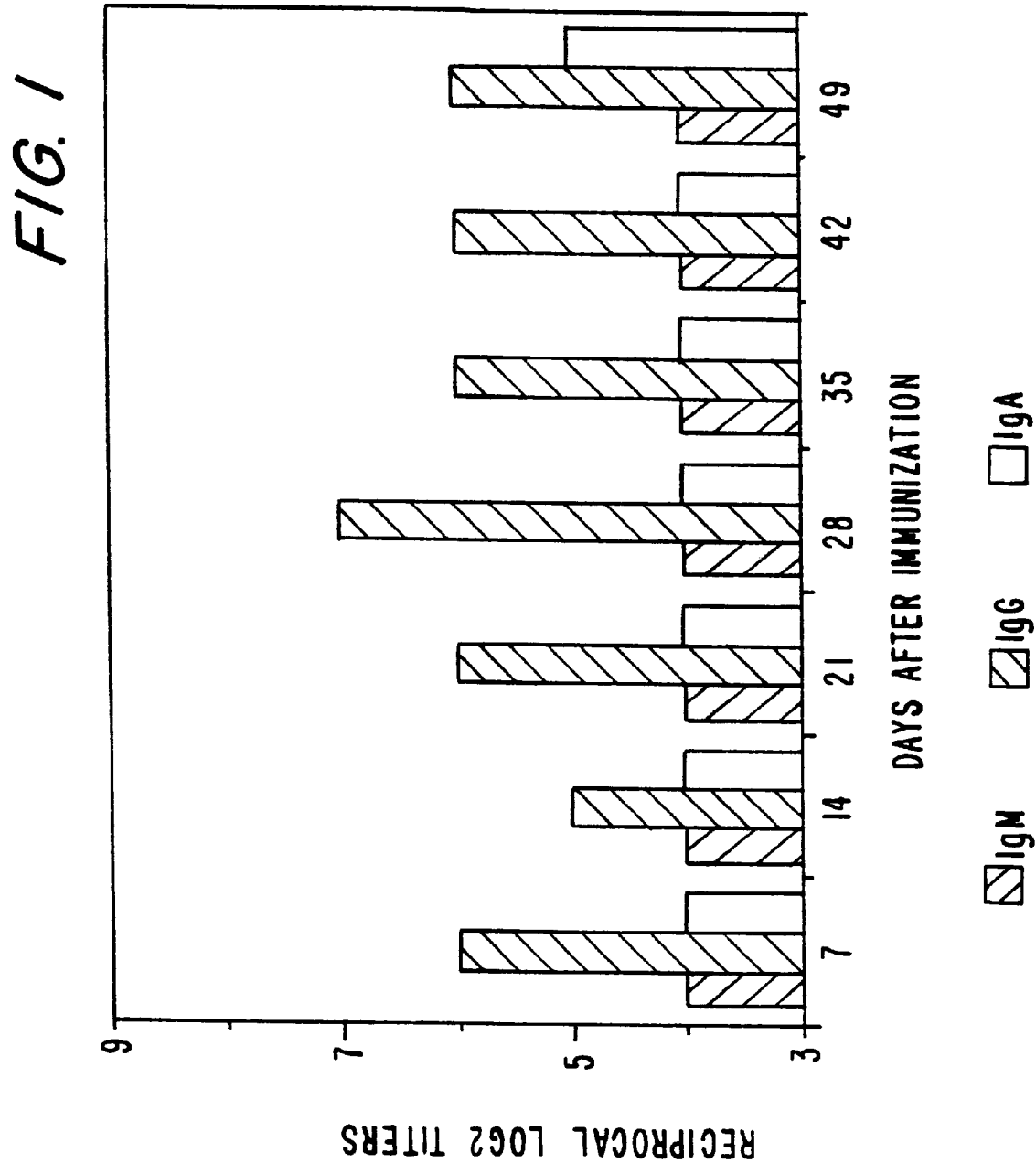

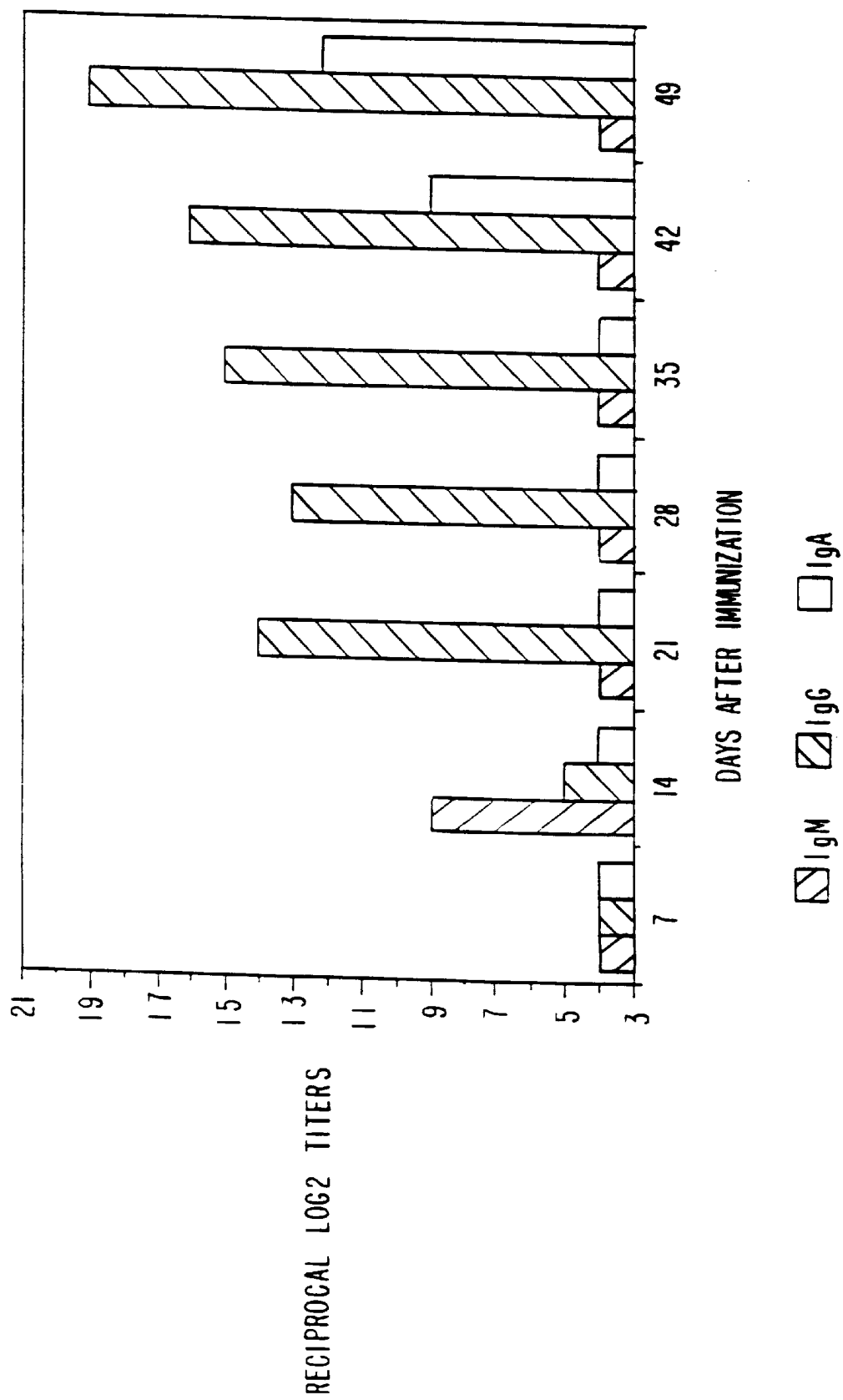

ORAL ADMINISTRATION OF PNEUMOCOCCAL ANTIGENS

REFERENCE TO RELATED APPLICATIONS

This application is a continuation-in-part of application Ser. No. 08/458,399, filed Jun. 2, 1995, incorporated herein by reference.

This application is a continuation-in-part of application Ser. No. 08/446,201, filed May 19, 1995 as a continuation-in-part of copending U.S. patent application Ser. No. 08/312,949, filed Sep. 30, 1994, which itself is a continuation-in-part of copending U.S. patent application Ser. No. 08/246,636 filed May 20, 1994, which itself is a continuation-in-part of copending U.S. patent application Ser. No. 08/048,896 filed Apr. 20, 1993 now abandoned, which itself is a continuation-in-part of copending U.S. patent application Ser. No. 07/835,698 filed Feb. 12, 1992 now abandoned, which itself is a continuation-in-part of U.S. patent application Ser. No. 07/656,773 filed Feb. 15, 1991 (now abandoned). The disclosure of each of such related applications is incorporated herein by reference.

FIELD OF THE INVENTION

This invention relates to oral immunization or administration of hosts, animals or humans, with pneumococcal antigens to stimulate an immunological response and preferably provide protection against pneumococcal infection, preferably against colonization, and more preferably against systematic infection; and, to compositions therefor.

Several publications are referenced in this application. Full citation to these references is found at the end of the specification immediately preceding the claims or where the publication is mentioned; and each of these publications is hereby incorporated herein by reference.

BACKGROUND OF THE INVENTION

Streptococcus pneumoniae causes more fatal infections world-wide than almost any other pathogen (Anonymous, 1991; Fraser, 1982). In the U.S.A., deaths caused by S. pneumoniae rival in numbers those caused by AIDS (Anonymous, 1991). In the U.S.A., most fatal pneumococcal infections occur in individuals over 65 years of age, in whom S. pneumoniae is the most community-acquired pneumonia. In the developed world, most pneumococcal deaths occur in the elderly, or in immunodeficient patents including those with sickle cell disease. In the less-developed areas of the world, pneumococcal infection is one of the largest causes of death among children less than 5 years of age (Berman et al., 1985; Greenwood et al., 1987; Spika et al., 1989, Bale, 1990). The increase in the frequency of multiple antibiotic resistance among pneumococci and the prohibitive cost of drug treatment in poor countries make the present prospects for control of pneumococcal disease problematical (Munoz et al., 1992; Marton et al., Klugman, 1990).

Humans acquire pneumococci through aerosols or by direct contact. Pneumococci first colonize the upper airways and can remain for weeks or months. As many as 50% or more of young children and the elderly are colonized. In most cases, this colonization results in no apparent infection (Gray et al., 1980; Gray et al., 1981; Hendley et al., 1975). Studies of outbreak strains have suggested that even highly virulent strains can colonize without causing disease (Smillie et al., 1938; Smillie et al., 1936; Gratten et al., 1980; DeMaria et al., 1984). These expectations have been recently confirmed using molecular probes to fingerprint individual clones (M. J. Crain, personal communication to one of the inventors). In some individuals, however, the carried organism can give rise to symptomatic sinusitis or middle ear infections. If pneumococci are aspirated into the lung, especially with food particles or mucus, they can cause pneumonia. Infections at these sites generally shed some pneumococci into the blood where they can lead to sepsis, especially if they continue to be shed in large numbers from the original focus of infection. Pneumococci in the blood can reach the brain where they can cause meningitis. Although pneumococcal meningitis is less common than other infections caused by these bacteria, it is particularly devastating; some 10% of patients die and greater than 50% of the remainder have life-long neurological sequelae (Bohr et al., 1985; Klein et al., 1981).

In elderly adults, the present 23-valent capsular polysaccharide vaccine is about 60% effective against invasive pneumococcal disease with strains of the capsular types included in the vaccine (Bolan et al., 1986; Shapiro et al., 1991). The 23-valent vaccine is not effective in children less than 2 years of age because of their inability to elicit adequate responses to most polysaccharides (Cowan et al., 1978; Gotschlich et al., 1977). Improved vaccines that can protect children and adults against invasive infections with pneumococci would help reduce some of the most deleterious aspects of this disease. A vaccine that protected against disease but did not reduce pneumococcal carriage rates would not, however, be expected to control the disease in immunocompromised individuals (Shapiro et al., 1991) and in unimmunized individuals. Such a vaccine would also not be expected to affect the rates of infection in immunized children prior to the development of an adequate antibody or immunological response.

A strategy that could control infections in all of these individuals would be any form of immunization that prevented or greatly reduced carriage, and hence transmission of pneumococci. In the case of immunization of young children with Haemophilus influenzae group b polysaccharide-protein conjugates, it has been observed that carriage is reduced from about 4% to less than 1%, (Barbour et al., 1993), a possible explanation of concomitant herd immunity (Chiu et al., 1994). If a vaccine could prevent colonization by pneumococci, such a vaccine would be expected to prevent virtually all pneumococcal infections in the immunized patients. Since even unimmunized patients must acquire pneumococci from others, a vaccine that reduced carriage should reduce infections in immunocompromised, as well as unimmunized patients. In fact, an aggressive immunization program, coupled with antibiotic treatment of demonstrated carriers, might be able to largely eliminate the human reservoir of this organism. It may not be possible, however, to totally eliminate pneumococci since there are a number of reports that they have been found in laboratory rodents (Fallon et al., 1988). Whether these pneumococci are infectious for man, easily transmittable to man, or even pathogens in wild rodents is not known. S. pneumoniae does not live free in the environment.

Although intramuscular immunization with capsular polysaccharide vaccines has been effective at reducing the incidence of pneumococcal sepsis in the elderly (Shapiro et al., 1991), it has not been reported to affect pneumococcal carriage rates in children up to 54 months of age (Douglas et al., 1986; Douglas et al., 1984). The principal determinant of specific immunity at mucosal surfaces is secretory IgA (S-IgA) which is physiologically and functionally separate from the components of the circulatory immune system.

Mucosal S-IgA response are predominantly generated by the common mucosal immune system (CMIS) (Mestecky, 1987), in which immunogens are taken up by specialized lympho-epithelial structures collectively referred to as musoca-associated lymphoid tissue (MALT). The term common mucosal immune system refers to the fact that immunization at any mucosal site can elicit an immune response at all other mucosal sites (Mestecky, 1987). Thus, immunization in the gut can elicit mucosal immunity in the upper airways and visa versa. The best studied MALT structures are the intestinal Peyer's patches (Mestecky, 1987). Further, it is important to note that oral immunization can induce an antigen-specific IgG response in the systemic compartment in addition to mucosal IgA antibodies (McGhee, J. R. and H. Kiyono 1993, "New perspectives in vaccine development: mucosal immunity to infections", *Infectious Agents and Disease* 2:55–73).

Most soluble and non-replicating antigens are poor mucosal immunogens, especially by the peroral route, probably because they are degraded by digestive enzymes and have little or no tropism for the gut associated lymphoid tissue (GALT). A notable exception is cholera toxin (CT). CT is a potent mucosal immunogen (Elson, 1989; Lycke et al., 1986; Wilson et al., 1989) probably because of the GM1 ganglioside-binding property of its binding subunit, CTB, that enables it to be taken up by the M cells of Peyer's patches and passed to the underlying immunocompetent cells. In addition to being a good mucosal immunogen, CT is a powerful adjuvant which greatly enhances the mucosal immunogenicity of other soluble antigens co-administered with it (Elson, 1989; Lycke et al., 1986; Wilson et al., 1989). Although it remains somewhat controversial, pure or recombinant CTB probably does not have these properties when administered intragastrically (i.g.) as an adjuvant. Very small amounts (<1 $\mu$g) of intact CT, however, can act synergistically with CTB as a powerful oral adjuvant (Wilson et al., 1990). This finding may account for apparent adjuvant activity of many commercial preparations of CTB that usually contain small amounts of contaminating CT.

The mechanisms by which CT and CTB act as adjuvants are not fully understood, but are certainly complex, and appear to depend on several factors including 1) the toxic activity associated with the ADT-ribosylating property of the A1 subunit (Abbas et al., 1991); 2) increased permeability of mucosae (Abbas et al., 1991; Ziegler-Heitbrock et al., 1992); 3) enhanced antigen-presenting cell function (with increased levels of IL-1) (Abbas et al., 1991; Ziegler-Heitbrock et al., 1992); as well as 4) direct stimulation of T and B cell activities (Elson, 1989; Lycke et al., 1986; Wilson et al., 1989; Wilson et al., 1990). This last point is controversial, however, as the in vitro effects of CT or CTB on T and B cells are generally inhibitory rather than stimulatory (Abbas et al., 1991). Nevertheless, numerous reports attest to the in vivo mucosal immunoenchancing effects of CT and of CTB coupled to antigens (Hakansson et al., 1994; Anderson et al., 1981; Liang et al., 1988; Dagen et al., 1995; Dillard et al., 1994; Szu et al. 1989). Recent studies have shown that orally-administered CT can induce Th2 type responses for antigen-specific serum IgG and mucosal IgA antibodies (Xu-Amano, J., H. Kiyono, R. J. Jackson, H. F. Staats, Fujihashi, P. D. Burrows, C. O. Elson, S. Pillai and J. R. McGhee. 1993, "Helper T cell subsets for immunoglobulin A responses: Oral immunization with tetanus toxoid and cholera toxin as adjuvant selectively induces Th2 cells in mucosa associated tissues", J. Exp. Med. 178:1309–1320, Xu-Amano, R. J. Jackson, K. Fujihashi, H. Kiyono, H. F. Staats and J. R. McGhee, 1994, "Helper Th1 and Th2 cell responses following mucosal or systemic immunization with cholera toxin", Vaccine 12:903–911). Recently Elson et al. have shown that CT selectively inhibits $CD8^+$ cells, and therefore tends to abrogate suppressive effects (Elson et al., 1995).

Since immunity to carriage would be expected to operate at the mucosal surface, any attempt to identify antigens for vaccines against carriage should include immunizations designed to elicit mucosal immune responses. Accordingly, the oral (including peroral, intragastric) immunization or administration with pneumococcal proteins, as in the present invention has not, it is believed, been heretofore disclosed or suggested or, in addition, the evaluation of adjuvants, as in the present disclosure, has not, it is believed, been heretofore taught or suggested.

SUMMARY OF THE INVENTION

In accordance with the present invention, it has now been surprisingly found that oral or peroral administration, preferably into the gut (e.g., stomach, intestines, digestive tract; intragastric), of pneumococcal surface protein A (PspA) or an immunogenic fragment thereof elicits an immunological response and can even provide protection to a host against pneumococcal infection such as colonization and/or systemic infection.

Accordingly, in one aspect, the present invention provides a method of protecting a host, preferably a human host, against pneumococci and/or systemic infection by oral or peroral administration to the host, preferably by administration into the gut (stomach, intestines, digestive tract; e.g., intragastrically) of the host, of an effective amount of at least one pneumococcal surface protein A (PspA) and/or an immunogenic fragment thereof containing at least one protection-eliciting epitope.

In another aspect, the present invention provides a method of eliciting an immunological response in a host against pneumococci and/or systemic infection by oral or peroral administration to the host, preferably administration into the gut (stomach, intestines, digestic tract; e.g., intragastrically) of the host, of an effective amount of at least one PspA and/or an immunogenic fragment thereof containing at least one epitope. More preferably, the response is protective and the epitope is protection-eliciting.

The PspA may be in the form of killed whole S. pneumoniae or a lysate of whole S. pneumoniae. Alternatively, the PspA may be in the form of purified isolated protein or a fragment thereof (individually and/or collectively, for purposes only of shorthand in this specification, "PspA") may be obtained from bacterial isolates or may be formed recombinantly. The PspA can be from in vivo expression thereof by a suitable vector containing DNA coding for PspA by recombinant techniques. The PspA is preferably in a vaccine or immunogenic composition. Such a composition can include a pharmaceutically acceptable adjuvant and/or a pharmaceutically acceptable carrier.

The PspA may be mixed with pharmaceutically acceptable excipients which are compatible with the PspA. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof.

In a preferred aspect of the invention, the PspA is administered with non-toxic amounts of cholera toxin as an adjuvant.

The oral administration preferably is effected by delivery into the stomach or gut, i.e., intragastrically to provide protection to the host against infection, preferably colonization, and more preferably against systemic infection. The oral administration also can provide protection to the host against pulmonary infection as well as protection to the host against an infection starting as a pulmonary infection. However, the oral administration can also involve respiratory mucosa, gingival mucosa or alveolar mucosa, and the administration can be perlingual or sublingual or into the mouth or respiratory tract, especially if the composition is administered in a liquid form, e.g., as a syrup, elixir etc. However, intragastric administration is preferred.

Thus, compositions of the invention especially for oral administration, are conveniently provided as liquid preparations, e.g., isotonic aqueous solutions, suspensions, emulsions, or viscous compositions which may be buffered to a select pH. However, since delivery to the digestive tract is preferred, compositions of the invention can be "solid" from the pills, tablets, capsules, caplets, and the like, including "solid" preparations which are time-release or which have a liquid filling, e.g., gelatin covered liquid, whereby the gelatin is dissolved in the stomach and/or small intestine for delivery into the gut and/or digestive system.

In a particular aspect of the invention, there is provided a method of immunization of a host against Streptococcus pneumoniae which comprises orally or perorally administering to the host an immunizing amount of pneumococcal surface protein A (PspA) in the form of a killed whole pneumococci, a lysate of pneumococci or an isolated PspA or an immunogenic fragment thereof.

The present invention further provides a vaccine composition or immunogenic composition for oral or peroral administration to a host, preferably for administration into the gut (stomach, digestive tract; e.g., intragastrically) of a host to confer protection or elicit an immunological response, against S. pneumoniae, which comprises:

an effective amount of a pneumococcal surface protein A (PspA) in the form of a killed whole pneumococci, a pneumococcal lysate, an isolated and purified PspA or an immunogenic fragment thereof containing at least one epitope, preferably protection-eliciting epitope, and optionally an adjuvanting amount of an adjuvant, preferably CT, and optionally a pharmaceutical carrier therefor.

Other objects and embodiments of the invention are disclosed in or are obvious variants from the following description.

BRIEF DESCRIPTION OF THE DRAWINGS

In the following description, reference is made to the accompanying Figures, wherein:

FIGS. 1 and 2 show bar graphs (Reciprocal Log2 ELISA (enzyme linked immunoadsorbant assay) Titers v. Days after immunization) of IgM, IgG and IgA responses of mice orally-immunized by gastric intubation with 7.5 μg of purified native PspA, with (FIG. 2) and without (FIG. 1) 10 μg/mouse CT, 7, 14, 21, 28, 35, 42 and 49 days after immunization (open bars=IgA, darkened bars=IgM, bars with diagonal stripes=IgG) (Log2=4 is just below the limit of detection of the assay. Thus, values of 4 should be considered as indicating that there was no detectable antibody).

DETAILED DESCRIPTION OF INVENTION

As discussed above, the principal determinant of specific immunity at mucosal surfaces is secretory IgA (S-IgA) which is physiologically and functionally separate from the components of the circulatory immune system. S-IgA antibody responses may be induced locally by the application of suitable immunogens to a particular mucosal site. The bulk of mucosal S-IgA responses, however, are the results of immunity generated via the common mucosal immune system (CMIS) (Mestecky, 1987), in which immunogens are taken up by specialized lympho-epithelial structures, collectively referred to as mucosa-associated lymphoid tissues (MALT). The best studied immunologic lympho-epithelial structures are the gut-associated lymphoid tissues (GALT), such as intestinal Peyer's patches (Mestecky, 1987). Other structurally and functionally similar lymphoid follicles occur at other mucosal surfaces, including those of the respiratory tract (Croitoru et al., 1994).

Bronchus-associated lymphoid tissue (BALT) was described by Bienenstock (Bienenstock et al., 1973a; Bienenstock et al. 1973b) in experimental animals, but is apparently not present in the noninfected human bronchial tree (Pabst, 1992). The upper respiratory tract in humans, however, is furnished with Waldeyer's ring of tonsils and adenoids. In rodents, the functional equivalent of these consists of nasal-associated lymphoid tissue (NALT), a bilateral strip of lymphoid tissue with overlying M-like epithelial cells at the base of the nasal passages (Kuper et al., 1992).

According to the present invention, a host can be effectively immunized by oral instillation (e.g., intragastric instillation) of bacterial protein immunogens, preferably PspA or a fragment thereof, preferably mixed with an adjuvant, more preferably cholera toxin (CT). Of course, as an adjuvant, the amount of cholera toxin used is non-toxic to the host.

The ability of a vaccine to protect against pneumococcal colonization, as provided herein, means that the active component may protect against disease not only in the immunized host but, by eliminating carriage among immunized individuals, the pathogen and hence any disease it causes may be eliminated from the population as a whole.

Oral or peroral administration (e.g., intragastric administration) can also prevent sepsis resulting from administration of pneumococci, so that the vaccine can protect against both pneumococcal colonization and sepsis (systemic infection).

As mentioned, PspA is the preferred antigen. WO 92/14488 is incorporated herein by reference. In published International patent application WO 92/14488, there are described the DNA sequences for the pspA gene from S. pneumoniae Rx1, the production of a truncated form of PspA by genetic engineering and the demonstration that such truncated form of PspA confers protection in mice to challenge with live pneumococci.

From sequences of the pspA gene, it has been shown that PspA proteins are variable in size (roughly 70 kDa). The C-terminal 37% of the molecule is largely composed of the 20-amino acid repeats which form a binding site that permits PspA to attach to the phosphcholine residues of the pneumococcal lipoteichoic acids. The central region of PspA is rich in prolines and is suspected to be the portion of the molecule that passes through the cell wall. The sequence of the N-terminal 80% of the molecule is largely α-helical and contains the region of PspA that can elicit antibodies that are protective against sepsis. Although PspA's are almost always at least slightly different from one another, there is enough cross-reactivity between them that antibodies or an immunological response to one PspA detect or is effective with respect to PspAs on all pneumococci. Moreover, immunization with one PspA can either protect against death or delay death with virtually all different challenge strains. Accordingly, a mixture of a small number of PspA's could provide effective immunity against most pneumococci.

The immunoprotective truncated PspAs described in WO 92/14488 may be used in the present invention as the PspA fragments described above for oral or peroral administration.

Numerous vector systems for in vitro and in vivo expression of recombinant proteins are known; e.g., bacterial systems such as E. coli; and virus systems such as bacterial viruses, poxvirus (vaccinia, avipox virus, e.g., canarypox virus, fowlpox virus), baculovirus, herpes virus; yeast; and the like; and, these systems may be used for producing recombinant PspA using the coding therefor or of WO 92/14488.

Immunogenicity can be significantly improved if the antigen (PspA) is co-administered with an adjuvant, commonly used as 0.001% to 50% percent solution in phosphate buffered saline. Adjuvants enhance the immunogenicity of an antigen (PspA) but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system. Adjuvants can also attract cells of the immune system to an antigen depot and stimulate such cells to elicit immune responses.

Immunostimulatory agents or adjuvants have been used for many years to improve the host immune response to, for example, vaccines. Intrinsic adjuvants, such as lipopolysaccarides, normally are the components of the killed or attenuated bacteria used as vaccines. Extrinsic adjuvants are immunomodulators which are typically non-covalently linked to antigens and are formulated to enhance the host immune response. Aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and, more recently, a HBsAg vaccine has been adjuvanted with alum.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. To efficiently induce humoral immune response (HIR) and cell-mediated immunity (CMI), immunogens are preferably emulsified in adjuvants.

Desirable characteristics of ideal adjuvants include any or all of:

(1) lack of toxicity;
(2) ability to stimulate a long-lasting immune response;
(3) simplicity of manufacture and stability in long-term storage;
(4) ability to elicit both CMI and HIR to antigens administered by various routes;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example IgA) against antigens.

U.S. Pat. No. 4,855,283 granted to Lockhoff et al. on Aug. 8, 1989 which is incorporated herein by reference thereto teaches glycolipid analogs including N-glycosylamides, N-glycosylureas and N-glycosylcarbamates, each of which is substituted in the sugar residue by an amino acid, as immune-modulators or adjuvants. Thus, Lockhoff et al. (U.S. Pat. No. 4,855,283) reported that N-glycolipids analogs displaying structural similarities to the naturally occurring glycolipids, such as glycosphingolipids and glycoglycerolipids, are capable of eliciting strong immune responses in both herpes simplex virus vaccine and pseudorabies virus vaccine. Some glycolipids have been synthesized from long chain alkylamines and fatty acids that are linked directly with the sugar through the anomeric carbon atom, to mimic the functions of the naturally occurring lipid residues.

U.S. Pat. No. 4,258,029 granted to Moloney, assigned to Connaught Laboratories Limited and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Octodecyl esters of aromatic amino acids completed with a recombinant hepatitis B surface antigen, enhanced the host immune responses against hepatitis B virus.

As previously mentioned, compositions of the invention, especially for oral administration, are conveniently provided as liquid preparations, e.g., isotonic aqueous solutions, suspensions, emulsions or viscous compositions which may be buffered to a selected pH. However, since delivery to the digestive tract is preferred, compositions of the invention can be in the "solid" form of pills, tablets, capsules, caplets and the like, including "solid" preparations which are time-released or which have a liquid filling, e.g., gelatin covered liquid, whereby the gelatin is dissolved in the stomach and/or small intestine for delivery to the gut and/or digestive system.

Compositions of the invention can contain pharmaceutically acceptable flavors and/or colors for rendering them more appealing. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion.

Liquid preparations are normally easier to prepare than gels and other viscous compositions, and solid compositions. Additionally, liquid compositions are somewhat more convenient to administer, especially to animals, children, particularly small children, and others who may have difficulty swallowing a pill, tablet, capsule or the like, or in multi-dose situations. Viscous compositions, on the other hand can be formulated within the appropriate viscosity range to provide longer contact periods with mucosa, such as the lining of the stomach or intestine.

Suitable nontoxic pharmaceutically acceptable carriers, and especially oral carriers, will be apparent to those skilled in the art of pharmaceutical and especially oral or peroral pharmaceutical formations. For those not skilled in the art, reference is made to the text entitled "REMINGTON'S PHARMACEUTICAL SCIENCE", 17th edition, 1985, incorporated herein by reference. Obviously, the choice of suitable carriers will depend on the exact nature of the particular dosage form, e.g., liquid dosage form [e.g., whether the composition is to be formulated into a solution, a suspension, gel or another liquid form, or solid dosage form [e.g., whether the composition is to be formulated into a pill, tablet, capsule, caplet, time release form or liquid-filled form].

Solutions, suspensions and gels, normally contain a major amount of water (preferably purified water) in addition to the antigen (PspA). Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to PspA. This will present no problem to those skilled in chemical and pharmaceutical principles, or problems can be readily avoided by reference to standard texts or by simple experiments (not involving undue experimentation), from this disclosure.

The immunologically effective compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular patient or animal, and the composition form used for administration (e.g., solid vs. liquid). Dosages for humans or other mammals can be determined without undue experimentation by the skilled artisan, from the Examples below (e.g., from the Examples involving mice).

When CT is used as an adjuvant for oral immunizations, specific IgA antibodies are induced in secretions. Strong circulatory immune responses can also be induced, with IgG and IgA antibodies in the serum, and IgG and IgA antibody-secreting cells in the spleen. The circulatory (or systemic) immune responses elicited by oral (peroral; intragastric) administration of PspA along with CT are comparable with, or even stronger than, those induced by the administration of similar immunogens by the intragastric (i.g., peroral) route (Wu et al., 1993; Russell et al. 1991). Accordingly, it appears that oral (peroral, i.g.) immunization is an effective route for stimulating common mucosal responses as well as circulatory antibody responses and can require less antigen than other immunization routes.

Most soluble or non-replicating antigens are poor immunogens, especially by the peroral route, probably because they are degraded by digestive enzymes and have little or no tropism for the GALT. A notable exception is CT, which is a potent mucosal immunogen (Elson et al., 1984), probably because of the $G_{M1}$ ganglioside-binding property of this binding subunit, CTB, that enables it to be taken up by the M cells of Peyer's patches and passed to the underlying immunocompetent cells. In addition to being a good mucosal immunogen, CT is a powerful adjuvant (Elson et al., 1989; Lycke et al., 1986; Wilson et al., 1989). When administered in μg does, CT greatly enhances immunogenicity of other soluble antigens co-administered with it.

CTB is a strong adjuvant when given orally or perorally (e.g., intragastrically) in mice along with antigen, but CTB has no direct adjuvant effect, but can act synergistically with CT (Wilson et al., 1990).

As discussed above, the mechanisms by which CT and CTB act as adjuvants are not fully understood, but are certainly complex, and appear to depend on several factors, including: 1) the toxic activity associated with the ADP-ribosylating property of the A1 subunit (Lycke et al., 1992; Abbas et al., 1991); 2) increased permeability of mucosae (refs. 46, 47, 48, 49). This last point is controversial, however, as the in vitro effects of CT or CTB on T and B cells are generally inhibitory rather than stimulatory (Woogen et al., 1987; Garrone et al., 1993; Haack et al., 1993; Quiding et al., 1991; Czerkinsky et al., 1989; Svernerholm et al., 1984). Nevertheless, numerous reports attest to the in vivo mucosal immunoenhancing effects of CT and of CTB couples to antigens (Lycke et al., 1986; Wilson et al., 1989; Abraham et al., 1991; Szu et al., 1989; Chen et al., 1990; Liang et al., 1988; Hakansson et al., 1994; Anderson et al., 1981; Dagen et al., 1995; Dillard et al., 1994). And, CT can selectively inhibit $CD8^+$ cells, and therefore tend to abrogate suppressive effects (Elson et al., 1995).

Although carriage of pneumococci can be maintained for long periods in the very young and the elderly, it is generally not a permanent condition. Carriage is much less common in older children and young adults (Gray et al., 1980; Gray et al., 1981; Hendley et al., 1975; Brimblecombe et al., 1958; Masters et al., 1958). One explanation for these findings is that carriage may be interfered with by immunity (possibly mucosal immunity) to pneumococci (Gray et al., 1980; Gwaltney et al., 1975). Most human saliva have IgA antibodies to type 23 capsular polysaccharide and phosphocholine (an immunodominant determinant of pneumococcal cell wall teichoic acids) (Russell et al., 1990). It seems likely, therefore, that human sera would also contain antibodies to other pneumococcal antigens. In the cases of group A streptococci, M proteins have been shown to be required for colonization in rats, and antibodies to M proteins can protect against colonization of the throat (Bessen et al., 1988; Hollingshead et al., 1993). In mice, the inventors have shown herein that immunity to PspA can prevent carriage of S. pneumoniae.

Antibodies may be effective against carriage in two ways, namely: 1) they might act at the mucosal surface by opsonizing pneumococci, preventing attachment or surface invasion; 2) they might act via opsonophagocytosis and killing. This latter mechanism could be especially important if carriage is dependent on minimal invasion of the nasal mucosal surface. The complement fixing antibodies could prevent the invasion and facilitate the killing of any pneumococci that invaded locally. Alternatively, complement fixing antibodies might be able to act and the mucosal surface if inflammation causes a sufficient release of complement, phagocytes, and possibly serum antibody.

One of these mechanisms might play a role in the observation that carriage of H. influenzae can be prevented by an intramuscular vaccine (Barbour et al., 1993). It has recently been reported that significant levels of H. influenzae polysaccharide-specific IgG and IgA are detected in secretions of children following immunization with the group b polysaccharide conjugate vaccine (Chiu et al., 1994; Kauppi et al., 1993).

Existing mouse protection data (Briles et al., 1989; Briles et al., 1981; Lock et al., 1988, Lock et al., 1992) suggests that antibodies that can opsonize pneumococci (e.g. those to the capsule) are generally more protective against sepsis than those that block the activities of toxins (e.g. pneumolysin) or enzymes (e.g. autolysin or neuraminidase). However, at the mucosal surface, the role played by antibodies that inactivate toxins and enzymes may be greater than that played by opsonic antibodies. The reason to suspect this is that for opsonic antibodies to exert their anti-bacterial effect, complement and phagocytes are required. Phagocytes are rare on the surface of normal nasopharyngeal tissue, and even if present, the phagocytes do not have the filtering action of the spleen and reticuloendothelial system to increase their chance of interactions with opsonized bacteria. Antibodies that block the virulence enhancing effects of pneumolysin and pneumococcal enzymes should be able to bind their antigens just as effectively whether phagocytes were present or not.

The results provided herein show that oral or peroral (e.g., i.g.) immunization with heat-killed pneumococci, and pneumococcal lysates, and purified PspA can protect mice against sepsis and therefore carriage too. As noted earlier, the ability of a vaccine to protect against disease not only in the immunized host, but, by eliminating carriage among immunized individuals, the pathogen and hence any disease it causes may be eliminated from the population as a whole.

The vaccine or immunogenic composition which is administered orally, perorally or intragastrically as provided herein may be formulated in any convenient manner and in a dosage formulation consistent with the mode of administration and the elicitation of a protective response (see discussion above and Examples below). The quantity of antigen to be administered depends on the subject to be immunized and the form of the antigen. Precise amounts and form of the antigen to be administered depend on the judgment of the practitioner. However, suitable dosage ranges are readily determinable by those skilled in the art from this disclosure, without undue experimentation, and may be of the order of micrograms to milligrams. Suitable regimes for initial administration and booster doses also are variable, may include an initial administration followed by subsequent administrations; but nonetheless, may be ascertained by the skilled artisan, from this disclosure, without undue experimentation.

The following Examples are provided for illustration and are not to be considered a limitation of the invention.

EXAMPLES

Example 1

Characterization of Immune Responses in Mice Orally Immunized with PspA

Prior to oral immunization, mice were deprived of food for two hours and then given a solution of sodium bicarbonate to neutralize stomach acid. Thirty minutes later, mice were orally-immunized by gastric intubation with 7.5 $\mu$g of purified native PspA with or without CT. Oral immunizations were carried out on day 0, 7, 14, and 35. Serum and fecal extracts were collected prior to immunization on days 7, 14 and 35. Sera and fecal pellets were also collected on days 21, 28, 42 and 49. Sera and fecal extracts were obtained and assayed as previously described (Jackson R. J., K. Fujihoski, J. Xu-Amano, H. Kiyono, C. O. Elson and J. R. McGhee. 1993. "Optimizing oral vaccines: induction of systemic and mucosal B. cell and antibody responses to tetanus toxoid by use of cholera toxin as an adjuvant", Infect. Immun. 61:4272–4279 de Vos et al., 1991). Additionally, the ability of oral immunization with PspA to elicit protective immunity was examined using the previously described mouse model of pneumococcal sepsis (Briles et al., 1992; Briles et al., 1989).

When mice were orally immunized with PspA alone, antigen-specific serum IgG responses were detected after the primary immunization. The Log2 titers were 5 to 7 (FIG. 1). These responses were not enhanced following the booster oral immunizations, and no IgM responses were detected during the analysis period (FIG. 1). No IgA antibody to PspA was detected until day 49 when the titer was only Log2–5. The fecal extracts had no detectable levels of antigen-specific responses.

When PspA was given orally with CT, antigen specific IgM, IgG, and IgA responses were induced in the serum. PspA-specific IgM antibodies Log2=9 were detected after the second injection. PspA-specific IgG responses were elevated to Log2=19 after the 4th oral immunization with PspA plus CT; Also, PspA-specific serum IgA responses of Log2=9 and 13 were detected on day 42 and 49, respectively (FIG. 2). Mucosal IgA responses in fecal extracts (Log2=5) were detected after the fourth immunization.

Example 2

Characterization of Protection Against Sepsis Elicited by Mice Immunized Orally within PspA Mice were challenged intravenously with $3.6 \times 10^3$ colony forming units (CFU) of S. pneumoniae A66 two weeks following the 4th oral immunization with PspA alone or PspA plus CT. The results (Table 1, below) demonstrated that oral immunization with purified PspA (using CT as an adjuvant) can provide systemic protective immunity to otherwise fatal infections with S. pneumoniae.

| Oral immunization with PspA using cholera toxin as an adjuvant induces protective immunity to systemic challenge with capsular type 3 strain A66 *Streptococcus pneumoniae* | | | |
|---|---|---|---|
| | Antigen used for immunization | | |
| | PspA + CT | PspA | None |
| Log$_2$ Reciprocal titer of IgG anti-PspA | 19 | 6 | <4 |
| Day of Death for individual mice | >21, >21, >21, >21 >21, >21, >21 | 1, 1, 2, 3, 4, >21 >21, >21 | 1, 1, 2, 2, 3 |
| Median Day of Death | >21 | 3.5 | 2 |
| Alive:Dead | 7:0 | 3:5 | 0:5 |
| P value vs. "None" | 0.003 | n.s. | |
| P value vs. "PspA" | 0.05 | | n.s. |

Note:
C57BL/6J Mice were challenged intravenously with $3.5 \times 10^3$ A66. P values shown above were calculated by the two tailed Wilcoxon two-sample rank test. Using the Kruskal-Wallis non-parametric analysis of variance the P value is 0.0071.

These results are analogous to providing humans with solid or solid-with-liquid-center forms which are absorbed primarily in the gut (i.e., swallowed whole for intragastric absorption), and are also indicative of the utility of liquid forms (which may be more advantageous for administration to children, especially children age 2 or less).

In summary of this disclosure, the present invention provides a method of immunizing a host or of stimulating an immunological response in a host against pneumococci and for protecting against systemic infection by pneumococci, by oral, particularly intragastric, administration of PspA in various forms.

Having thus described in detail preferred embodiments of the present invention, it is to be understood that the invention defined by the appended claims is not to be limited by particular details set forth above, as many apparent variations thereof are possible without departing from the spirit or scope thereof.

REFERENCES

1. Abbas, A. K., Lichtman, A. H., Pober, J. S., In Cellular and Molecular Immunology, ed. Wonsiewicz M., (W.B. Saunders Co., Philadelphia) (1991).

2. Abraham, E., Robinson, A., Vaccine 9:757–764 (1991).

3. Anastassiou, E. D., Yamada, H., Francis, M. L., Mond, J. J., Tsokos, G. C., J. Immunol. 145:2375–2380 (1990).

4. Andersson, B., Eriksson, B., Falsen, E., Fogh, A., Hansen, A., Nylen, O., Peterson, H., and Svanborg-Eden, C., Infect. Immun. 32:311–317 (1981).

5. Anonymous. Centers for Disease Control HIV/AIDS Surveillance Report, August: 1–18 (1991).

6. Bale, J. R., Rev. Infect. Dis. 12 (Suppl 8):S861–S1083 (1990).

7. Barbour, M. L., Mayon-White, R. T., Crook, D. W., Coles, C., Moxon, E. R., ICAAC Abstracts 33:175 (1993).

8. Berman, S., McIntosh, K., Rev. Infect. Dis. 7:647–691 (1985).

9. Bessen, D., Fischetti, V. A., Infect. Immun. 56:2666–2672 (1988).

10. Bienenstock, J., Johnston, N., Perey, D. Y., Lab. Invest. 28:686–692 (1973a).

11. Bienenstock, J., Johnston, N. Perey, D. Y., Lab. Invest. 28:693–698 (1973b).

12. Bohr, V., Rasmussen, N., Hansen, B., Gade, A., Kjersem, H., Johsen, N., Paulson, O., J. Infect. Dis. 10:143–157 (1985).

13. Bolan, G., Broome, C. V., Facklam, R. R., Plikaytis, B. D., Fraser, W. D., Schlech, W. F. I., Ann. Intern. Med. 104:1–6 (1986).

14. Briles, D. E., Crain, M. J., Gray, B. M., Forman, C., Yother, J., Infect. Immun. 60:111–116 (1992).

15. Briles, D. E., Claflin, J. L., Schroer, K., Forman, C., Nature 294:88–90 (1981).

16. Briles, D. E., Forman, C., Horowitz, J. C., Volanakis, J. E., Benjamin, W. H. Jr., McDaniel, L. S., Eldridge, J., Brooks, J., Infect. Immun. 57:1457–1464 (1989).

17. Brimblecombe, F. S. W., Cruicshank, R., Masters, P. L., Reid, D. D., Stewart, G. T., British Medical Journal:119–128 (1958).

18. Bromander, A., Holmgren, J., Lycke, N., Journal of Immunology 146:2908–2914 (1991).

19. Chen, K.-S., Strober, W., Eur. J. Immunol., 20:433–436 (1990).

20. Chiu, S. S., Greenberg, P. D., Marcy, S. M., Wong, V. K., Chang, S. J., Chiu, C. Y., Ward, J. I., Pediatric Res. Abstracts 35:10A (1994).

21. Converse, G. M. III, Dillon, H. C. Jr., J. Clin. Micro. 5:293–296 (1977).

22. Cowan, M. J. Ammann, A. J., Wara, D. W., Howie, V. M., Schultz, L., Doyle, N., Kaplan, M., Pediatrics 62:721–727 (1978).

23. Croitoru, K., Bienenstock, J., In Handbook of Mucosal Immunology, ed. Ogra, P. L., Mestecky, J., Lamm, M. E., Strober, W., McGhee, J. R., Bienenstock, J., (Acamdemic Press, Inc., San Diego, Calif.) pp. 141–149 (1994).

24. Czerkinsky, C., Russell, M. W., Lycke, N., Lindbald, M., Holmgren, J., Infect. Immun. 57:1072–1077 (1989).

25. Czerkinsky, C., Nilsson, L-A., Nygren, H., Ouchterlony, O., Tarkowksi, A., J. Immunol. Methods 65:109–121 (1983).

26. Dagen, R., Melamed, R., Abranson, O., Piglansky, L., Greenberg, D., Mendelman, P. M., Bohidar, N., Ter-Minassian, D., Cvanovich, N., Lov, D., et al., Pediat. Res. 37:172A (1995).

27. de Vos, T., and Dick, T. A., J. Immunol. Med. 141:285–288 (1991).

28. DeMaria, T. F., McGhee, R. B., Lim, D. J., Arch. Otolaryngol. 110:279–280 (1984).

29. Dillard, J. P. and Yother, J., Molec. Microbiol. 12:959–972 (1994).

30. Douglas, R. M., Miles, H. B., Paton, J. C., American Journal of Diseases of Children 140:1183–1185 (1986).

31. Douglas, R. M. Miles, H. B., Journal of Infectious Diseases 149:861–869 (1984).

32. Elson, C. O., Curr. Topics Microbiol. Immunol. 146:29–33 (1989).

33. Elson, C. O., Ealding, W., J. Immunol. 132:2736–2741 (1984).

34. Elson, C. O., Holland, S. P., Dertzbaugh, M. T., Cuff, C. F., A. O., Anderson, J. Immunol. 154:1032–1040 (1995).

35. Fallon, M. T., Reinhard, M. K., Gray, B. M., Davis, T. W., Lindsey, J. R., Laboratory Animal Science 38:129- (1988).

36. Francis, M. L., Ryan, J., Jobling, M. G., Holmes, R. K., Moss, J., Mond, J. J., Journal of Immunology 148:1999–2005 (1992).

37. Fraser, D. W., In Bacterial Vaccines, ed. J B Robbins, Hill J C, Sadoff J C, (New York) xix–xxiv (1982).

38. Garrone, P., Banchereau, J., Molecular Immunology 30:627–635 (1993).

39. Gizurarson, S., Tamura, S., Kurata, T., Hasiguchi, K., Ogawa, H., Vaccine 9:825–832 (1991).

40. Gotschlich E. C., Goldschneider, I., Lepow, M. L., Gold, R., In Antibodies in human diagnosis and therapy (Raven, N.Y.) pp. 391–402 (1977).

41. Gratten M. Naraqi, S., Hansman, D., Lancet ii:192–195 (1980).

42. Gray, B. M. Converse G. M. III, Dillon, H. C., J. Infect. Dis. 142:923–933 (1980).

43. Gray, B. M., Converse, G. M. III, Huhta, N., Johnston, R. B. Jr., Pichichero M. E., Schiffman, G., Dillon, H. C. Jr., J. Infect. Dis. 142:312–318 (1981).

44. Greenwood, B. M., Greenwood A. M., Bradley, A. K., Tulloch, S., Hayes, R., Oldfield, F. S. J., Ann. Trop. Pediatr. 7:91–99 (1987).

45. Gwaltney, J. W., Sande, M. A., Austrian, R., et al., J. Infect. Dis. 132:62 (1975).

46. Haack, B. M., Emmrich, F., Resch, K., Journal of Immunology 150:2599–2606 (1993).

47. Hakansson, A., Kidd, A., Wadell, G., Sabharwal, H., and Svanborg, C., Infect. Immun. 62:2707–2714 (1994).

48. Hendley, J. O., Sande, M. A., Stewart, P. M., et al., J. Infect. Dis. 132:55 (1975).

49. Hollingshead, S. K., Simecka, J. W., Michalek, S. W., Infect. Immun. 61:2277–2283 (1993).

50. Kauppi, M., Eskola, J. Kathty, H. H., ICAAC Abstracts 33:174 (1993).

51. Klein, J. O., Rev. Infect. Dis. 3:246-(1981).

52. Klugman, K. P., Clin. Microbiol. Rev. (1990).

53. Kuper, C. F., Koornstra, P. J., Hameleers, D. M. H., Biewenga, J., Spit, B. J., Duijvestijn, A. M., van Breda Vriesman, P. J. C., Sminia, T., Immunol. Today 13:219–224 (1992).

54. Liang, X., Lamm, M. E., Nedrud, J. G., Journal of Immunology 141:1495–1501 (1988).

55. Lock, R. A., Hansman, D., Paton, J. C., Microbial Pathogenesis 12:137–143 (1992).

56. Lock, R. A., Paton, J. C., Hansman, D., Microb. Pathog. 5:461–467 (1988).

57. Lycke, N., Holmgren, J., Immunology 59:301–308 (1986).

58. Lycke, N., Strober, W., J. Immunol. 142:3781–3787 (1989).

59. Lycke, N., Karlsson, U., Sjölander, A., Magnusson, K-E., Scand. Journal of Immunology 33:691–698 (1991).

60. Lycke, N., Tsuji, T., Holmgren, J., European Journal of Immunology 22:2277–2281 (1992).

61. Marton, A., Gulyas, M., Munoz, R. Tomasz, A., J. Infect. Dis. 163:542–548 (1991).

62. Masters, P. L., Brumfitt, W., Mendez, R. L., Likar, M., Brit. Med. J. 1:1200–1205 (1958).

63. Mestecky, J., J. Clin. Immunol. 7:265–276 (1987).

64. Munoz, R., Musser, J. M., Crain, M. Briles, D. E., Marton, A., Parkinson, A. J., Sorensen U., Tomasz, A., Clinic Infect. Dis. 15:112–118 (1992).

65. Muñoz, E., Zubiaga, A. M., Merrow, M., Sauter, N. P., Huber, B. T., J. Exp. Med. 172:95–103 (1990).

66. Pabst, R., Immunology Today 13:119–122 (1992).

67. Quiding, M., Nordstrom, I., Kilander, A., Anderson, G., Hansen, L. A., Holmgren, J., Czerkinsky, C., J. Clin. Invest. 88:143–148 (1991).

68. Russell, M. W., Prince, S. J., Ligthart, G. J., Mestecky, J., Radl, J., Aging Immunol. Infect. Dis. 2:275–286 (1990).

69. Russell, M. W., Wu, H-Y., Infection and Immunity 59:4061–4070 (1991).

70. Shapiro, E. D., Berg, A. T., Austrian, R., Schroeder, D., Parcells, V., Margolis, A., Adair, R. K., Clemmens, J. D., N. Engl. J. Med. 325:1453–1460 (1991).

71. Smillie, W. G., Am. J. Hyg. 24:522–535 (1936).

72. Smillie, W. G., Warnock, G. H., White, H. J., Am. J. Pub. Hlth. 28:293–302 (1938).

73. Spika, J. S., Munshi, M. H., Wojtyaniak, B., Sack, D. A. Hossain, A., Rahman, M., Saha, S. K., Ann. Trop. Pediatr. 9:33–39 (1989).

74. Svernerholm, A. M., Jertborn, M., Gothefors, L., Karim, A. M. M. M., Sack, D. A., Holmgren, J., J. Infect. Dis. 149:884–893 (1984).

75. Szu, S. C., Li, X., Schneerson, R., Vickers, J. H., Bryla, D., Robbins, J. B., Infect. Immun. 57:3823–3827 (1989).

76. Wilson, A. D., Clarke, C. J., Stokes, C. R., Scand. J. Immunol. 31:443–451 (1990).

77. Wilson, A. D., Stokes, C. R., Bourne, F. J., Scand. J. Immunol. 29:739–745 (1989).

78. Wilson, A. D., Bailey, M., Williams, N. A., Stokes, C. R., European Journal of Immunology 21:2333–2339 (1991).

79. Woogen, S. D., Ealding, W., Elson, C. O., Journal of Immunology 139:3764–3770 (1987).

80. Wu, H-Y, Russell, M. W., Infection and Immunity 61:314–322 (1993).

81. Ziegler-Heitbrock, H. W. L., Passlick, B., Kafferiein, E., Coulie, P. G., Izbicki, J. R., Infect. Immun. 60:1692–1694 (1992).

What is claimed is:

1. A method of immunization of a host against pneumococcal infection to elicit a protective immunological response, which comprises orally administering to the host an immunizing amount of a composition comprising a pneumococcal component wherein the pneumococcal component consists essentially of isolated pneumococcal surface protein A (PspA) or at least one isolated fragment of said PspA, wherein said PspA or fragment thereof contains at least one protection-eliciting epitope.

2. The method of claim 1 wherein said pneumococcal component consists essentially of isolated and purified PspA.

3. The method of claim 1 wherein said composition includes an adjuvant.

4. The method of claim 3 wherein the adjuvant is cholera toxin.

5. The method of claim 1 wherein said pneumococcal component consists essentially of said fragment of PspA.

6. The method of claim 1 wherein said pneumococcal component consists essentially of said PspA.

7. The method of claim 1 wherein said oral administration is effected intragastrically.

8. A method of immunization of a host against Streptococcus pneumoniae to elicit a protective immunological response which comprises intragastrically administering to the host an immunizing amount of a composition comprising a pneumococcal component wherein the pneumococcal component consists essentially of isolated pneumococcal surface protein A (PspA) in the form of an isolated and purified PspA or an isolated fragment thereof, said PspA or fragment thereof containing at least one protection-eliciting epitope.

9. The method of claim 8 wherein said composition includes an adjuvant.

10. The method of claim 9 wherein the adjuvant is cholera toxin.

11. The method of claim 8 wherein said composition contains said PspA and an adjuvanting amount of cholera toxin.

12. The method of claim 8 wherein the pneumococcal component consists essentially of said PspA.

13. A method for eliciting an immunological response in a host against Streptococus pneumoniae which comprises orally administering to the host an effective amount of a composition comprising a pneumococcal component wherein said pneumococcal component consists essentially of isolated pneumococcal surface protein A (PspA) or at least one isolated fragment of said PspA containing at least one protection-eliciting epitope.

14. The method of claim 13 wherein the orally administering is performed by intragastrically administering and, the PspA is an isolated and purified PspA, or an immunogenic fragment thereof, wherein said PspA contains at least one protection-eliciting epitope.

* * * * *

UNITED STATES PATENT AND TRADEMARK OFFICE
CERTIFICATE OF CORRECTION

PATENT NO. : 6,232,116 B1
DATED : May 15, 2001
INVENTOR(S) : David E. Briles et al.

It is certified that error appears in the above-identified patent and that said Letters Patent is hereby corrected as shown below:

<u>Title page,</u>
Item [73], Assignee, change "University of Alabama at Birmingham Research Foundation" to -- UAB Research Foundation --.

<u>Claim 13,</u>
Line 2, change "Streptococus" to -- streptococus --.

Signed and Sealed this

Sixteenth Day of April, 2002

Attest:

JAMES E. ROGAN
*Director of the United States Patent and Trademark Office*

*Attesting Officer*